United States Patent [19]
Bailey et al.

[11] 4,326,540
[45] Apr. 27, 1982

[54] SYRINGE DEVICE WITH MEANS FOR SELECTIVELY ISOLATING A BLOOD SAMPLE AFTER REMOVAL OF CONTAMINATES

[75] Inventors: Donald L. Bailey, Thornton, Colo.; Charles Williams, Rolling Hills Estate, Calif.

[73] Assignee: Marquest Medical Products, Inc., Englewood, Colo.

[21] Appl. No.: 91,393

[22] Filed: Nov. 6, 1979

[51] Int. Cl.$^3$ .............................................. A61B 5/14
[52] U.S. Cl. ............................. 128/763; 128/218 PA
[58] Field of Search ............ 128/763, 765, 766, 218 P, 128/218 PA, 760, 238, 218 S, 218 R, 234; 222/386

[56] References Cited
U.S. PATENT DOCUMENTS

| | | | |
|---|---|---|---|
| 3,354,882 | 11/1967 | Coanda | 128/218 P |
| 3,943,917 | 3/1976 | Johansen | 128/763 |
| 3,985,122 | 10/1976 | Topham | 128/765 |
| 4,020,831 | 5/1977 | Adler | 128/765 |
| 4,133,304 | 1/1979 | Bailey | 128/764 |
| 4,206,768 | 6/1980 | Bailey | 128/763 |
| 4,212,309 | 7/1980 | Moorehead | 128/765 |

FOREIGN PATENT DOCUMENTS 1566602 12/1967 Fed. Rep. of Germany.

Primary Examiner—Kyle L. Howell
Attorney, Agent, or Firm—Gary M. Polumbus

[57] ABSTRACT

A syringe device has a hollow tubular body that receives a plunger, having in combination a handle portion rotatable within a sealing member portion, for obtaining gas-free blood samples. After an interior chamber of the syringe body is filled with blood under the influences of an individual's blood pressure, a seal is selectively established to isolate the sample. The syringe body is open at one end to receive the plunger and frictionally receives a hypodermic needle through a cylindrical end element disposed at the other end. A pair of linearatly extending seal interrupters, sliced from the handle portion of the plunger, extend from a position fixed on the handle portion across the sealing member to establish breach points, which in turn allow air communication between the interior chamber and the atmosphere. A pair of grooves disposed longitudinally near the open end of the syringe body retain the seal interrupters and prevent permanent indentations from forming in the sealing member while in storage.

8 Claims, 9 Drawing Figures

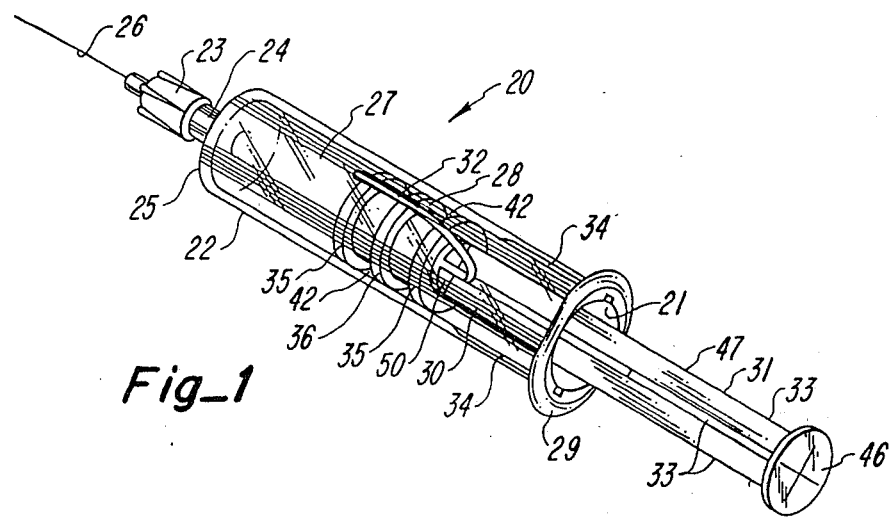
Fig_1
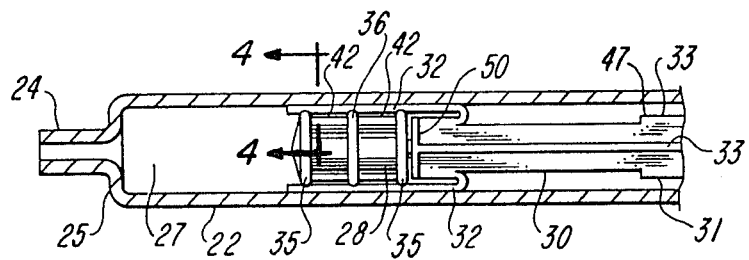
Fig_2
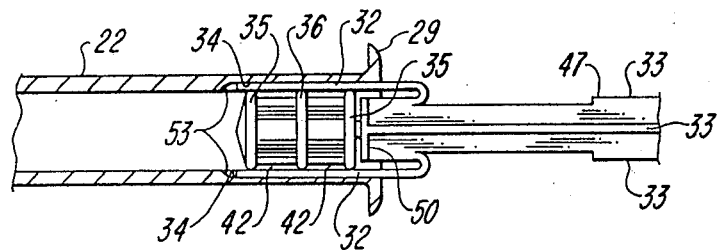
Fig_3
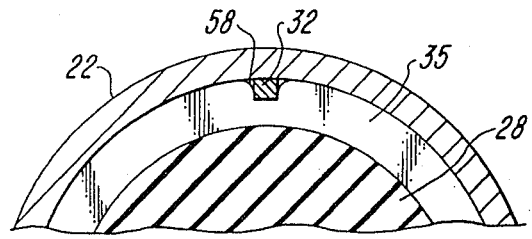
Fig_4

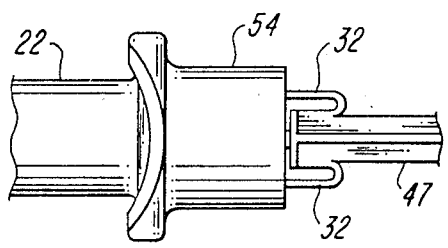
Fig_8
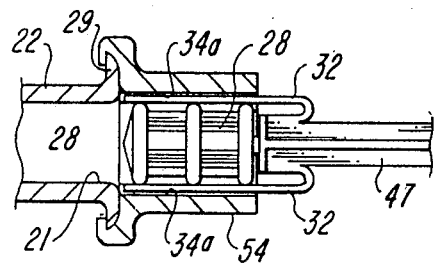
Fig_9
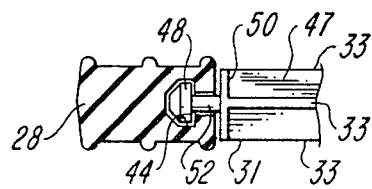
Fig_5
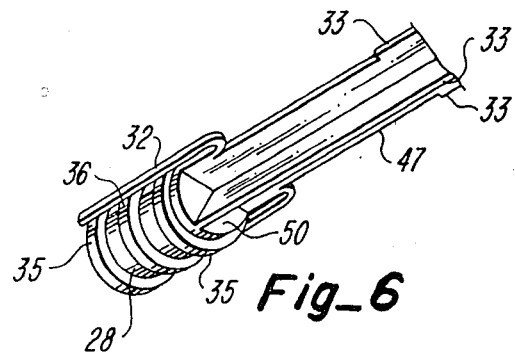
Fig_6
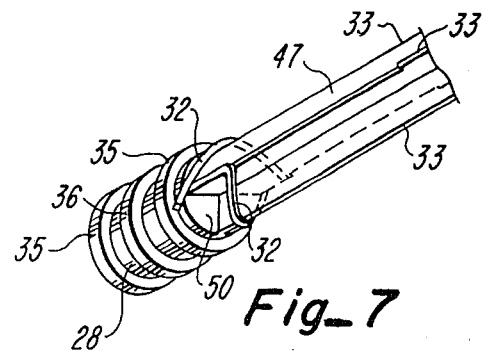
Fig_7

SYRINGE DEVICE WITH MEANS FOR SELECTIVELY ISOLATING A BLOOD SAMPLE AFTER REMOVAL OF CONTAMINATES

BACKGROUND OF THE INVENTION

1. Field of Invention

This invention relates to syringes for collecting blood samples, and more particularly syringes of the type that are used in drawing blood samples free of gaseous contaminates for use in blood gas analysis.

2. Description of the Prior Art

Syringe type devices are typically used for obtaining blood samples to perform blood gas analysis, which is an important diagnostic tool. Unfortunately, by the time a sample is withdrawn, treated with a liquid anticoagulant like heparin, and deposited for analysis, air and contaminates from the anticoagulant solution effect results when conventional syringes are used. One such blood collecting syringe is shown in U.S. Pat. No. 4,020,831 to Adler. Adler shows a holder and a plug which is so constructed that once the sample within the holder is placed in the centrifuge the plug seeks a level intermediate the densities between plasma and cell portions of the blood sample collected. No attempt is made to purge air from the sample.

Another syringe for collecting blood is shown in Johansen, U.S. Pat. No. 3,943,917 which discloses various types of structure for indenting a plunging sealing portion to allow communication between the interior chamber and the atmosphere so that a patient's blood pressure works to fill the interior chamber.

Currently the available syringes for obtaining a gas-free blood sample are disclosed in my pending U.S. Patent application for a SYRINGE DEVICE WITH MEANS FOR SELECTIVELY ISOLATING A BLOOD SAMPLE AFTER REMOVAL OF CONTAMINATES, Ser. No. 952,994, Filed Oct. 20, 1978, now U.S. Pat. No. 4,206,768, and U.S. Pat. Nos. 3,978,846 and 4,133,304, of which I am also the inventor. My pending application shows a plunger having a handle rotatable within and with respect to a dual circumferentially lipped sealing member. A thread or the like is extended across the sealing lips to interrupt the seal and is attached to the plunger handle. Once an individual's blood pressure fills the interior chamber of the syringe body, the seal interrupter can be wound onto the plunger handle to isolate a gas-free blood sample. Simultaneous treatment of the sample collected with an anticoagulant such as heparin is shown in my pending application, Ser. No. 50,970, filed June 22, 1979.

OBJECTS AND SUMMARY OF THE INVENTION

The principle object of the present invention is to provide a syringe device capable of utilizing the blood pressure of an individual to obtain a gas-free blood sample for blood gas analysis.

A related object of the present invention is to provide a syringe that can be stored in a ready to use form for long periods of time without affecting performance.

A further object of the present invention is to simplify collection of a gas free blood sample.

Another and further object of the present invention is to simplify the manufacture of syringes for obtaining gas-free blood samples.

In accordance with the objects of the present invention, a syringe with a tubular body has a trailing or open end which slideably receives a plunger consisting of a handle and a sealing member, the handle being rotatably connected to the sealing member about the longitudinal axis of the tubular body. The leading end of the tubular body frictionally receives a hypodermic needle through a short cylindrical end element having a bore therethrough so that the needle extends longitudinally away from the main tubular body. Once the hypodermic needle penetrates a vein or artery, blood passes through the central bore of the cylindrical portion and into an interior chamber defined by the interior of the tubular body and the forwardmost portion of the sealing member.

The handle of the plunger is preferably of X-shaped cross section and made of a machinable or moldable material. A pair of seal interrupters are formed by cutting shavings off opposite edges of the handle and bending the shavings 180°, back so that they can extend across the sealing member. The sealing member has an enlarged diameter circular lip at either end and an intermediate circular lip disposed between the end lips. All lips are of sufficient diameter to contact the interior wall of the main tubular body and form an hermetic seal therewith. The seal interrupters form two breach paths across the sealing member at the locations where they cross the sealing member lips.

Formed near the trailing or open end of the syringe body are two identical diametrically opposed grooves adapted to receive the seal interrupters in such a manner that they do not deflect the sealing member lips downward. In this manner the syringe device can be stored for extended periods of time without deformation occurring in the elastomer material from which the sealing member is formed.

BRIEF DESCRIPTION OF THE DRAWINGS

FIG. 1 is a perspective view of the syringe device of the invention.

FIG. 2 is a fragmentary longitudinal section of the tubular body of the invention with the sealing member and seal interrupters located within the tubular body shown in full and ready for use.

FIG. 3 is a fragmentary section of the tubular body of the invention with the sealing member and seal interrupters adjacent the storage grooves shown in full.

FIG. 4 is an enlarged fragmentary section taken along line 4—4 of FIG. 2.

FIG. 5 is an enlarged longitudinal section of the sealing member with the handle portion shown in full.

FIG. 6 is a fragmentary perspective view of the sealing member and handle with the seal interrupters in position to obtain a blood sample.

FIG. 7 is a fragmentary perspective similar to FIG. 6 with the seal interrupters positioned after a blood sample has been obtained.

FIG. 8 is an enlarged fragmentary elevation of an alternative embodiment of the invention.

FIG. 9 is an enlarged fragmentary longitudinal section of an alternative embodiment of the invention.

DESCRIPTION OF THE PREFERRED EMBODIMENT

Referring to FIG. 1, a preferred form of a syringe 20 of the present invention includes a transparent or translucent main tubular body 22 of circular transverse cross section having an open trailing or rearward end 21, surrounded by an annular flange 29, and a reduced diameter end element or neck 24 protruding axially away from a leading or forward end wall 25 of the tubular body to which a hypodermic needle 26 is frictionally connected by a needle connector 23 in an hermetically sealed relation. The neck 24 is hollow and communicates with an interior chamber 27, generally defined by the space in the tubular body 22, the leading end wall 25 and a plunger 30 which is received in the tubular body 22 through the open trailing end 21. The plunger 30 includes a plunger handle 31 and a resilient sealing member 28 which are rotatably connected. Both the plunger handle and sealing member are received through the open trailing end 21 of the tubular body. The sealing member 28 is further adapted to slide along the interior surface of the main tubular body 22 in a sealed relationship therewith.

The plunger handle 31 is of X-shaped cross section and made of a semi-rigid material such as polypropylene. A pair of seal interrupters 32, are shaved from two of the four edges 33 of the plunger handle 31 and bent 180° rearwardly in such a fashion so as to extend along opposite sides of the sealing member 28. Near the trailing end 21 of the syringe body, diametrically opposed grooves 34, of substantially the same length as the sealing member 28, are formed in the interior surface of the syringe body 22. A flake of heparin (not shown) which may be prepared in a manner as described in my copending U.S. application Ser. No. 50,970 filed June 22, 1979, can be placed in the interior chamber 27. Blood entering the interior chamber is thus immediately treated with a dry crystalline anticoagulant, such as heparin, so that the blood gas analysis test is unaffected by coagulation.

The sealing member 28 is constructed of a material having elastic and resilient properties such as rubber. In its undeformed shape, the sealing member 28 is generally cylindrical with a circular lip 35 at either end and an intermediate lip 36 disposed between the end lips. The lips 35 and 36 are of sufficient diameter to contact the interior surface of the syringe body 22 and form an hermetic seal therewith. A pair of toroidal void spaces 42 are defined between the cylindrical wall of the sealing member 28, the lips 35 and 36 and the internal surface of the main tubular body 22. The void spaces 42 are adapted to trap excess blood that flows past the sealing member's forwardmost lip 35. These spaces thus act as an overflow reservoir in permitting a larger amount of blood to flow past the interior chamber 27 and insure that all contaminates are purged from the interior chamber when a blood sample is drawn. Alternatively, when the user of the syringe is not necessarily watching as closely as might be hoped for, these void spaces 42 allow for a relatively large amount of blood to collect before there is any problem with the blood getting beyond the rearwardmost lip 35 and causing a problem with respect to cleanliness.

The handle 31 is elongated having a disc 46 on the trailing end, an intermediate body portion 47 of X-shaped cross section and a disc 50 near the leading end. A small diameter pin 52 forms a reduced diameter forward extension of the intermediate body 47 and a relatively small disc 48 is disposed on the leading end of the pin 52. Pin 52 and disc 48 are shaped to fit rotatably within a recess 44 in the trailing end of the sealing member 28 as shown in FIG. 5. The two seal interrupters 32 may be machined from two opposed edges 33 of the soft plastic, such as propylene, from which the intermediate body portion 47 is formed. These seal interrupters are filaments of the polypropylene that are adapted to extend from the living hinge connection near the leading end of the intermediate body portion 47 across all three sealing lips 35 and 36 of the sealing member 28. As the seal interrupter 32 crosses the lips of the sealing member 28, a breach or space 58 is formed between the sealing member 28 and the syringe body 22 as shown in FIG. 4.

As mentioned previously, the handle 31 is rotatably received within the sealing member 28. The disc 48 and pin 52 combined with the mating shape of the recess 44 allow the sealing member to be moved axially within the syringe body 22 by the handle 31. The circular configuration of the disc 48 and the mating recess 44 permits rotational movement of the handle relative to the sealing member for a purpose to be described later.

The hypodermic needle 26 is connected to the syringe 20 at the end fitting 24 in a manner well known in the art. The entire syringe and parts thereof are made of sterilizable materials so that they can be sterilized before use. Preferably the materials are so inexpensive that the syringe can be disposed of after use.

The grooves 34 have at the leading ends thereof, a converging chamfer 53 (FIG. 3). This chamfer 53 helps feed or drive the seal interrupters 32 into the desired positions forming breach points 58 in the sealing member 28 as the plunger 30 is pushed into the tubular body. The grooves 34 permit the syringe 20 to be stored, with the sealing member 28 entirely within the tubular body 22 for an indefinite time without deforming the sealing member 28.

Plastic syringe bodies are widely accepted throughout the medical industry. In a plastic syringe body the grooves 34 can be formed or molded inexpensively in the syringe body 22. If a glass syringe body 22 is utilized, the expense of forming the groove in glass dictates that an adaptor 59 made of plastic material be utilized (FIG. 9). The adaptor 59 fits over the outwardly protruding flanges 29 of the syringe body in a frictional grip. The adapter 54 has a bore therethrough allowing communication between the adapter and the tubular body 22, so that the sealing member 28 can be inserted into the tubular body when the syringe 20 is ready for use.

OPERATION AND ASSEMBLY

In the preferred embodiment the diametrically opposed seal interrupters 32 are placed across the sealing member 28. The seal interrupters are then aligned with the grooves 34 and inserted into the tubular body 22 of the syringe 20. The sealing member is left in the position adjacent to the grooves 34 during storage or shipment so that the seal interrupters 32 do not deflect and permanently deform the sealing lips 35 and 36.

When it is desired to take a blood sample, the plunger 30 is advanced to a position along the tubular body, which is marked in cc's of volume corresponding to the volume of the sample desired. The hypodermic needle 26, which is already connected to the end element 24 of the tubular body 22 by a needle connector 23, is then inserted into an artery or vein of the individual whose blood is to be tested. Communication between the hypodermic needle, the end element and the interior chamber 27 allows blood to fill the interior chamber. Once the level of blood has risen to a position where it fills the entire interior chamber, the operator rotates the handle 31 of the plunger 30 relative to the sealing member 28 thereby winding the seal interrupters 32 onto the plunger and closing the breach points 58 on the lips 35 and 36 (FIG. 8). Preferably, no blood is allowed to pass the trailing sealing lip 35 where it might create problems with cleanliness. It will be appreciated that as the blood fills the interior chamber 27, the chamber is purged of all gaseous materials that might contaminate the blood sample. Inclusion of a heparin flake, as previously described, will automatically treat the blood sample with an anticoagulant so that the blood sample may be tested at a later time.

As has previously been described in my prior application Ser. No. 952,994, when the syringe 20 is used in a donor having an extremely low blood pressure, such pressure being insufficient to completely fill the interior chamber 27 of the syringe in a short period of time, the sealing member is preset at a level of approximately 0.1 cc to 0.2 cc and an amount of blood sufficient to fill the reduced volume interior chamber is allowed to flow into the chamber. Once blood is observed in the void between the lips 35 and 36 of the sealing member 28, the plunger intermediate body 47 is rotated to establish a seal, as has previously been described in operations relative to individuals of higher blood pressure and the sealing member is withdrawn to create a low pressure zone to draw blood into the interior chamber until the desired volume of blood is in the syringe. Again, it will be appreciated that the blood sample obtained will be free of contaminates so that the blood gas analysis which may be performed on the sample will be undistorted.

It will be understood that changes may be made in the details of construction, arrangement and operation of the invention without departing from the spirit of the invention, particularly as it is defined in the following claims.

What is claimed is:

1. A syringe device for drawing blood samples comprising:
   a tubular body having an interior surface defining an elongated interior chamber, said tubular body having one open end and an end member at the opposite end, said end member having a bore therethrough defining means for connection to a hypodermic needle;
   a plunger slideably positioned within said tubular body, said plunger including an intermediate body portion extending out the open end of said tubular body and a resilient sealing member operatively connected to said intermediate body capable of establishing an hermetic seal with said interior surface of said tubular body;
   at least one flexible seal interrupter, said seal interrupter being generally linear and attached to said intermediate body adapted to interrupt said hermetic seal by being placed between said sealing member and the interior of said tubular body;
   at least one longitudinal groove extending along the interior surface of the tubular body having a chamfer at the forwardmost end thereof and said groove being positioned along the slideable path of said seal interrupter so that said seal interrupter can be positioned in the groove without interrupting the seal between the sealing member and the interior surface of the tubular body; and
   means for moving said seal interrupter into a position where it lies across and breaks the seal between the sealing member and said interior surface, and into a position wherein said seal is restored to prevent fluid flow past said sealing member.

2. The invention defined in claim 1 wherein there are two seal interrupters diametrically opposed from each other, attached to said intermediate body of said plunger.

3. The invention defined in claim 1 wherein said seal interrupters are an integral filament of the intermediate body of the plunger shaved from said body, said seal interrupter filament being adapted to be turned 180° so as to cross the sealing member.

4. The invention defined in claim 2 wherein there is a longitudinal groove in the tubular body for each seal interrupter.

5. A syringe device for drawing blood samples comprising:
   a tubular body having an interior surface defining an elongated interior chamber, said tubular body having one open end and an end member at the opposite end, said end member having a bore therethrough defining means for connection to a hypodermic needle;
   a plunger slideably positioned within said tubular body, said plunger including an intermediate body portion of X-shaped cross section extending out of the open end of said tubular body and a resilient sealing member operatively connected to said intermediate body capable of establishing an hermetic seal with said interior surface of said tubular body;
   at least one flexible seal interrupter formed by shaving an edge of the intermediate body, said seal interrupter being generally linear and remaining attached to said intermediate body, said seal interrupter being adapted to be bent backwardly 180° opposite the direction from which said seal interrupter was shaved from the intermediate body to thereby cross the sealing member of said plunger and break the seal between said sealing member and the interior surface of said tubular body; and
   means for removing said seal interrupting means from the position wherein they cross said sealing member to restore the hermetic seal and thereby prevent fluid flow past said sealing member.

6. The invention defined in claim 1 wherein said means for moving said seal interrupters to restore the hermetic seal includes a rotatable connection between said intermediate body and said sealing member.

7. The invention defined in claim 5 wherein said means for moving said seal interrupter to restore the hermetic seal includes a rotatable connection between said intermediate body and said sealing member.

8. The invention as defined in claim 5 wherein:
   said tubular body has an annular flange around the circumference of the open end; and
   a generally cylindrical hollow adapter configured to clasp said annular flange, said adapter having a longitudinal groove disposed along the hollow interior of said adapter.

* * * * *